Figure 1:
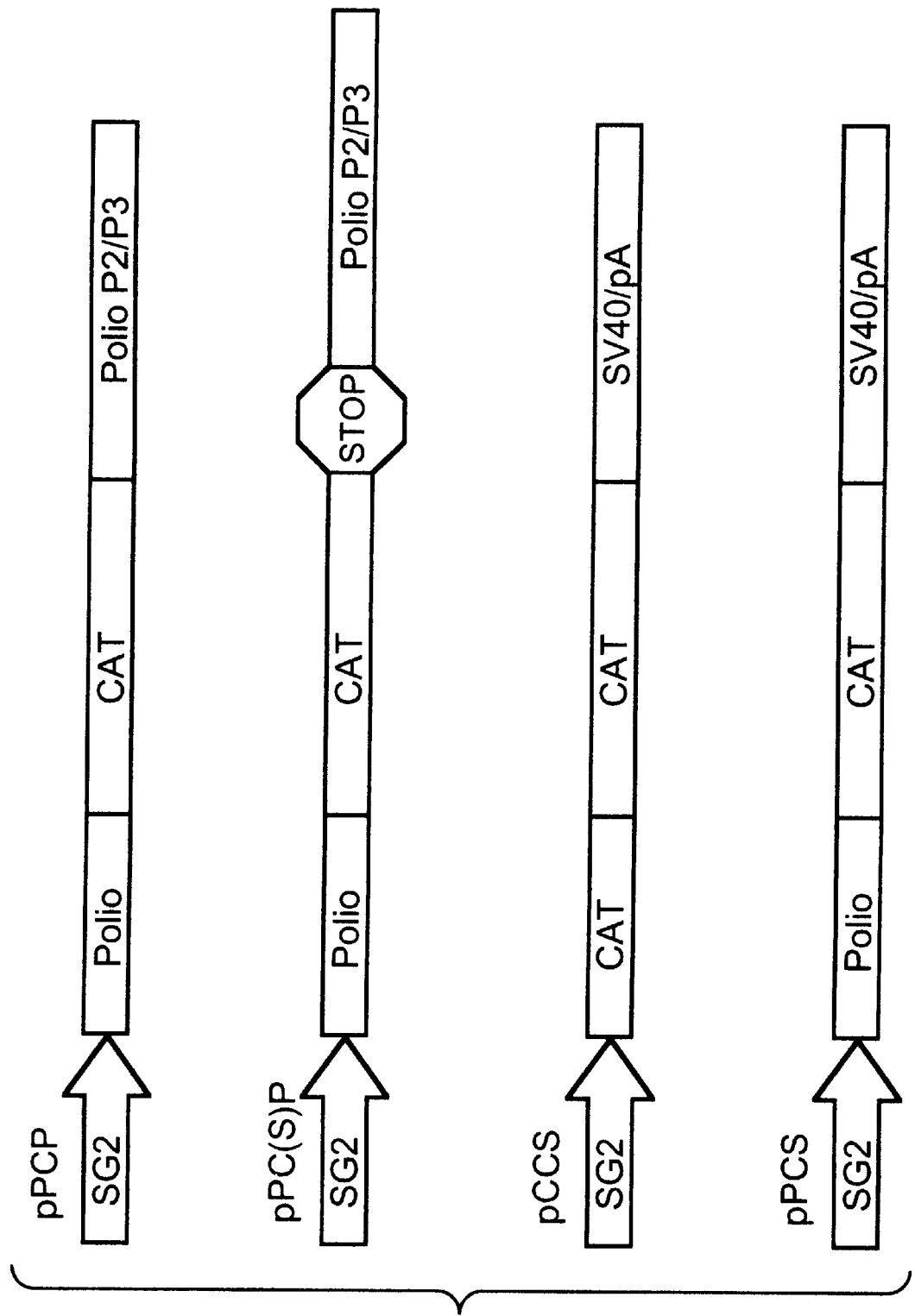

United States Patent [19]
Andrews et al.

[11] Patent Number: 6,156,538
[45] Date of Patent: Dec. 5, 2000

[54] HETEROLOGOUS GENE EXPRESSION WITH POLIOVIRUS REPLICON

[76] Inventors: David W. Andrews, 29 Reginald Street, Hamilton, Ontario, Canada, L8P 3X8; Martin J. G. Hughes, 23, Lydalls Road, Didcot, Oxfordshire, OX11 7HX, United Kingdom; Andrew D. Murdin, 146 Rhodes Circle, Newmarket, Ontario, Canada, L3X 1V2

[21] Appl. No.: 09/145,455

[22] Filed: Sep. 2, 1998

[51] Int. Cl.⁷ .......................... C12N 15/63; C12N 15/86; C12N 5/10; C12P 21/00
[52] U.S. Cl. ................... 435/69.1; 536/23.72; 536/24.1; 435/320.1; 435/353; 435/358; 435/364; 435/367; 435/371; 435/455
[58] Field of Search .............................. 435/320.1, 235.1, 435/69.1, 353, 358, 364, 367, 371, 455; 536/2.72, 24.1

[56] References Cited

U.S. PATENT DOCUMENTS 5,789,245   8/1998   Dubensky et al. ................... 435/320.1

OTHER PUBLICATIONS

Mattion et al, Journal of Virology, 68(6): 3925–3933, Jun. 1994.
Alexander et al, AIDS Research and Human Retroviruses, 10 (sup. 2): S57–S60, 1994.
Anderson et al, Virology 219: 140–149, 1996.
Filmus et al, Nucleic Acids Research, 20(11): 2755–2760, 1992.

*Primary Examiner*—Mary E. Mosher

[57] ABSTRACT

The replication machinery of polio virus is used to express heterologous gene products, such as chloramphenicol acetyl transferase, in mammalian cells. Detectable expression following DNA transfection demonstrated that a polio replicon containing a foreign gene in the P1 region transcribed from an inducible promoter can be exported from the nucleus to the cytoplasm. The proteins in the P2/P3 region of the RNA can be translated and thereby render the RNA capable of replication. A stable cell line harbouring the polio replicon in the genome results in constitutive expression of chloramphenicol acetyl transferase or other heterologous gene product.

17 Claims, 3 Drawing Sheets

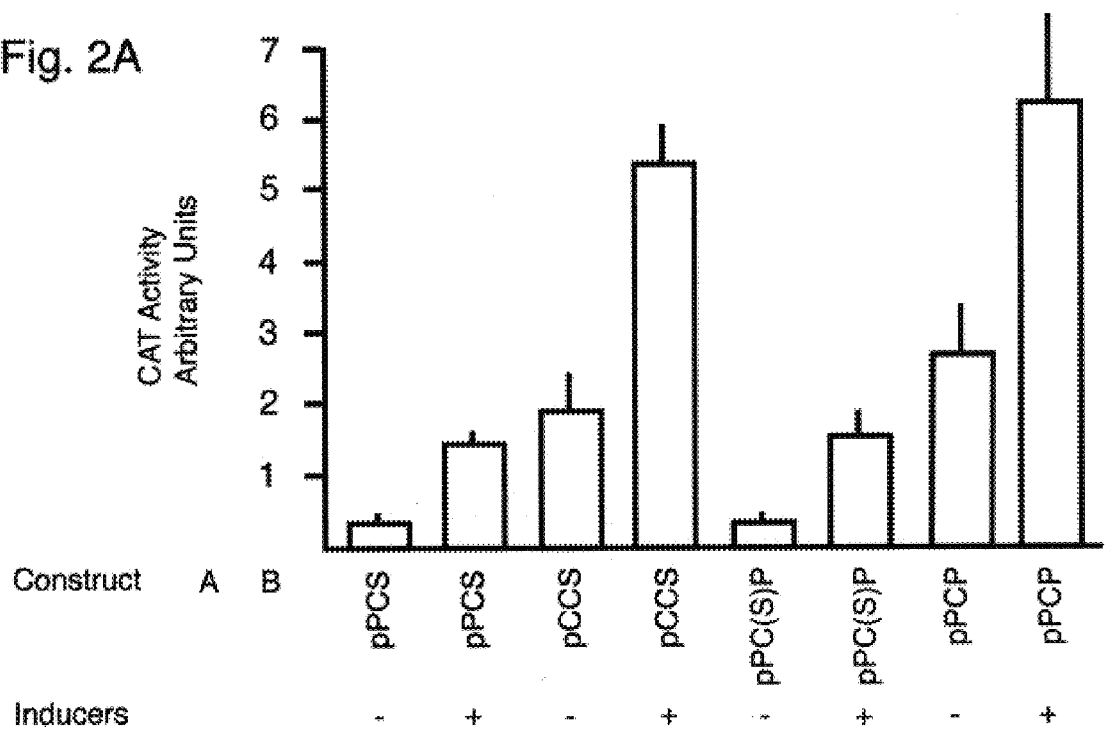
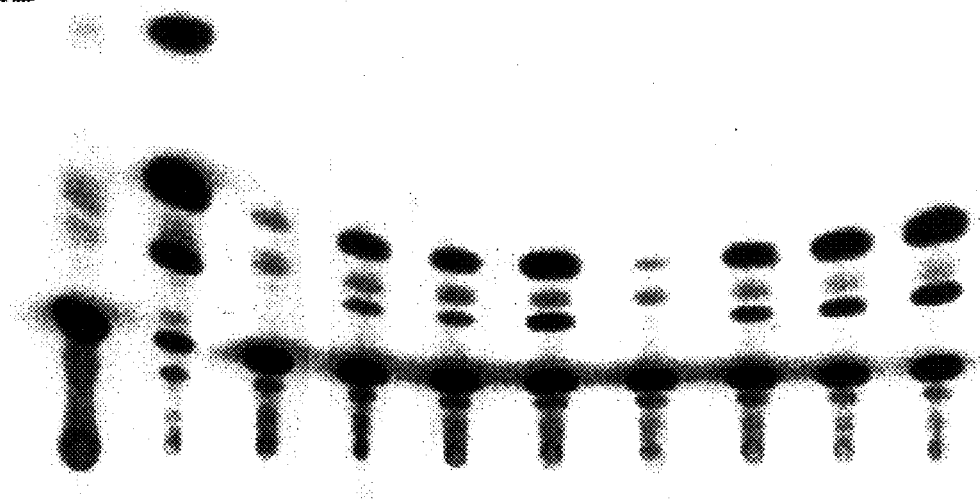

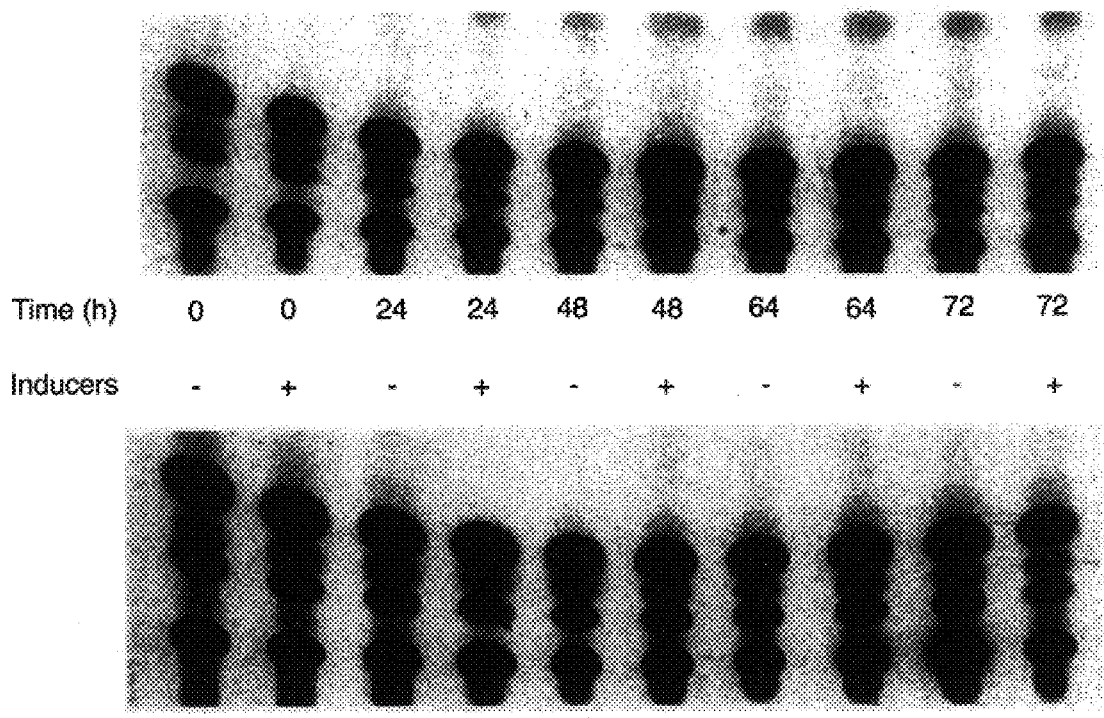

SEQUENCE LISTING

```
<160> NUMBER OF SEQ ID NOS: 1

<210> SEQ ID NO 1
<211> LENGTH: 18
<212> TYPE: DNA
<213> ORGANISM: Enterovirus sp.

<400> SEQUENCE: 1
gatcttgcgc ccggcccg                                                    18
```

HETEROLOGOUS GENE EXPRESSION WITH POLIOVIRUS REPLICON

FIELD OF INVENTION

The present invention relates to heterologous gene expression in mammalian cells using poliovirus replicon elements.

BACKGROUND TO THE INVENTION

Poliovirus is an enterovirus, a gene of the family Picornaviridae. The structure of the poliovirus is known, and is highly conserved among strains and serotypes.

The polio virus genome exists as a single-stranded RNA molecule of approximately 7,500 nucleotides. The RNA is comprised of three regions; a 5'untranslated region of 743 nucleotides, an open reading frame of 6,618 nucleotides, and a 3'untranslated region of 72 nucleotides followed by a terminal poly (A) tail (Refs 1, 2—various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure). The open reading frame can be further subdivided into the P1, P2 and P3 regions. The genes found in the P1 region encode for the capsid proteins. These genes can be deleted without effecting the ability of the viral RNA to translate or replicate (ref. 3). The P2 and P3 regions (encoding the non-structural proteins) (ref. 1) and features of the 5' untranslated region are essential for replication and translation (refs. 4, 5, 6, 7).

The ability to remove the structural P1 genes from the viral genome without compromising the ability of the RNA to replicate has been used both to study the mechanisms of replication and encapsidation (refs. 4, 5) and to produce foreign proteins whose genes have been placed in the P1 position. These include various Human Immunodeficiency Virus proteins (refs. 8, 9, 10), Simian Immunodeficiency Virus proteins (ref. 11) and carcinoembryonic antigen (ref. 12).

Most studies of polio virus (including those mentioned above) have been carried out by transfecting cells with RNA synthesised in vitro using bacteriophage T7 RNA polymerase (ref. 13). The reasoning behind this activity has been that polio virus does not, during a normal infection, enter the nucleus, and the RNA does not, therefore, undergo splicing or other nuclear processing events. It has been suggested that the polio RNA sequence contains adventitious splicing and polyadenylation signals which could negatively affect the RNA (ref. 13). Further, since the RNA would be embedded as part of a potentially larger primary transcript, biologically active, replication competent molecules may not be produced (ref. 13). In contrast, one early report demonstrated that infectious polio virus particles could be obtained by transient transfection of cell lines with plasmids harbouring cDNA copies of the polio virus genome (ref. 14). It is, however, unclear whether a cDNA containing the coding sequence for a foreign protein in place of the polio structural genes will generate an exportable transcript capable of replication when positioned behind a mammalian promoter. Although it is possible to construct replicons from RNA harbouring foreign genes, this system has the disadvantage that it is difficult to accurately check the sequence which has been transfected into cells, given the inherent infidelity of the RT-PCR reaction. This can be a particular concern when the proteins to be produced are to be subsequently used for human vaccination.

Transfection of cells with DNA encoding the polio replicon harbouring a foreign gene would allow for easy recovery and confirmation of transfected sequences. Moreover, DNA is inherently more stable and easier to work with than RNA. Finally, self replicating RNAs may be particularly useful when examining the regulation of a weak promoter. The potential problems of producing quantities of potentially toxic proteins, including the non-structural proteins of polio, could be overcome by the use of a suitably tight and inducible mammalian promoter system. Coupled to such a promoter, the polio replicon system may allow for rapid and high level increases in protein amounts post induction.

SUMMARY OF INVENTION

In the present invention, the replication machinery of poliovirus is used to express gene products heterologous to polio virus. DNA constructs containing an inducible mammalian promoter and the foreign gene in the P1 region of polio virus are used to transfect mammalian cells for foreign gene expression.

It is not essential that this system be under an active transcription promoter, since the replicon machinery amplifies the transcript in vivo. The relatively tightly controlled metallothionine/glucocorticoid system (ref. 15) is used as a representative mammalian promoter. To demonstrate the feasibility of this system for the synthesis of a foreign protein, the reporter protein, chloramphenicol acetyl transferase (CAT), was examined in transiently transfected cell lines, and a stable, transfected cell line was established. The transiently expressed constructs demonstrated that CAT was synthesised from a polio replicon when the P2/P3 protein were translated, demonstrating the feasibility of foreign gene expression.

Accordingly, in one aspect of the present invention, there is provided a DNA molecule, comprising, in sequence from the 5' end to the 3' end of the molecule, an inducible mammalian promoter, at least one functional portion of a 5'-untranslated region of a poliovirus which provides replication and translation, a gene encoding a gene product heterologous to poliovirus, and at least one functional portion of the P2 and P3 coding regions and the 3'UTR regions of poliovirus forming a functional replicon.

The inducible mammalian promoter may be a metallothionine gene (hMT-IIA) having inserted therein at least two glucocorticoid responsive elements (GREs), as described, for example, in U.S. Pat. No. 5,559,027 and ref. 15.

The linked GRE's may each comprise a synthetic molecule containing the consensus GRE sequence and having a positive strand having the nucleotide sequence:

5'-GATCTTGCGCCCGGCCCG-3'(SEQ ID NO: 1)

The two native constitutive elements of hMT-IIA, AP1 and AP2, located between bases −79 and −129 of the native hMT-IIA promoter, may be deleted. Additionally, the at least two GREs may be inserted at the SacII site (base −175) of the native hMT-IIA promoter, thereby disrupting a second constitutive element at that location.

The functional portion of the 5'-untranslated region of the poliovirus may be any portion functionally directing replication and translation of the foreign gene and the poliovirus replicon. The functional portion preferably comprises the complete 743 nucleotides of the 5'-untranslated region of the poliovirus.

The heterologous gene product which is expressed by the DNA molecule may be any protein or peptide and may comprise an enzyme, an antigen, an immunogen, an allergen, an enzyme inhibitor, a hormone, a lymphokine, an immunoglobulin or fragment thereof, a toxin, a toxin subunit, a structural protein or a receptor.

The functional poliovirus replicon may comprise any DNA sequence encoding a functional replicon fragment to permit RNA production and export for translation. Preferably the poliovirus replicon comprises the 5'UTR and the P2 and P3 coding regions and the 3'UTR.

The invention includes, in another aspect thereof, a vector for heterologous gene expression comprising the DNA molecule provided herein. The vector may have the identifying characteristics of pPCP.

The invention further extends, in an additional aspect of the invention, to an expression system for heterologous gene expression, comprising mammalian cells containing the vector provided herein for effecting expression of the heterologous gene product. The mammalian cells may be any convenient cells, such as Vero, CHO, HeLa, RatII or epithelial cells. The mammalian cells may be transiently or stably infected by the vector.

In a further aspect of the invention, there is provided a method of effecting heterologous gene expression, which comprises constructing a vector as provided herein; transfecting mammalian cells with the vector; effecting expression of the heterologous gene product from the mammalian cells; and recovering the heterologous gene product. The cells may be transiently or stably infected by the vector, which may have the identifying characteristics of pPCP.

BRIEF DESCRIPTION OF DRAWINGS

FIG. 1 shows the polio replicon containing constructs used in the experiments reported in the Examples below. The Chloramphenicol Acetyl Transferase (CAT) reporter gene was fused at the 3' end of either the Polio 5'UTR (pPCP, pPC(S)P and PPCS) or the CAT 5'UTR (pCCS). The CAT coding sequence was followed by either the sequence coding the polio virus P2/P3 region (pPCP and PPC(S)P) or the SV40 3'UTR and polyadenylation signal (pPCS and pCCS). A human metallothionine/glucocorticoid responsive promoter, SG2, was placed proximal to the 5'UTR. The constructs were inserted into the pGEM7Zf(−) (Promega) plasmid backbone.

FIG. 2, comprising upper (A) and lower (B) panels, illustrates CAT activity obtained from cell extracts following transient transfection with plasmids designed to test the activity of a DNA encoded polio replicon. Vero cells were transfected with (A) pGEM7Zf(−)(Promega), (B) PCMV-CAT, a constitutive, high level expressing plasmid, or the constructs shown in FIG. 1. Transcription was induced by the addition (+) of 5 mM $CdCl_2$ and 5 mM dexamethasone where indicated. Cell extract was prepared after harvesting the cells, 24 hours after induction. The extract was assayed for CAT activity using a standard thin layer chromatographic method (ref. 16).

FIG. 3, comprising panels A and B, illustrates that CAT expression from Vero cells stably transformed with plasmid pPCP is constitutive. Cells from either 6 passages (panel A) or 20 passages (panel B) following the establishment of a stable cell line were assayed for CAT activity at time points with or without induction by adding 5 mM $CdCl_2$ and 5 mm dexamethasone, as described for FIG. 2.

GENERAL DESCRIPTION OF INVENTION

By the experiments reported in the Examples below, the feasibility of transfecting cells with plasmids containing a foreign gene embedded within a polio replicon has been demonstrated. The data demonstrates that, under the control of a mammalian promoter, RNA can be produced from a nuclear-encoded gene. This RNA can be exported into the cytoplasm in a form in which the RNA replicative machinery remains operative. However, in order to regulate this system, it is necessary to have a promoter which can be maintained, very efficiently, in an "off" state.

A small amount of basal transcription is sufficient to allow the export to sufficient RNA to allow the polio replicative system to operate and overcome the low level of expression from the promoter. The polio replicon system provided herein can, with an efficiently regulated promoter, be used to transfect mammalian cells for the overproduction of proteins and peptides encoded by the foreign gene.

The use of plasmids to transfect the cells, also enables the user to easily recover the DNA for sequencing, thus confirming unambiguously the precise sequence of the expressed protein. The ability to amplify the signal by RNA replication may also prove useful for analyzing expression from very weak promoter sequences.

As seen below, it is possible to produce a cell line which stably expresses a reporter-gene containing polio replicon from plasmid encoded DNA. Expression remains unchanged for many passages. However, a "tighter" transcription promoter system, such as the tetracyclin-repressor system (ref. 18) may be necessary to create a stably transfected cell line which may be used for regulated expression of a gene of interest using a polio replicon system.

EXAMPLES

Example 1

This Example illustrates the construction of plasmids.

A series of DNA plasmids were constructed to examine the possibility that a polio-replicon-embedded foreign gene could be expressed in mammalian cells following DNA transfection. Shown in FIG. 1, these plasmids consisted of a combination of the 5'UTR from either polio or CMV, followed by the CAT coding region and one of either the 3'UTR and polyadenylation signal from SV40 virus, the polio P2/P3 regions separated from the CAT region by a stop/frameshift signal, or the polio P2/P3 regions in frame with the CAT gene. These fusions were all cloned into a pGEM7Zf(−) (Promega, Madison, USA) based plasmid vector, into which the SG2 inducible metallothionine/glucocorticoid promoter (ref. 15) had been cloned, with restriction endonuclease recognition sites positioned to allow the insertion of 5'UTR-CAT-3'UTR replicon constructs as PacI to BamHI fragments.

The basic construct, pPCP (FIG. 1) consisted of the complete 5'UTR from polio virus, fused at an NcoI site to the 5' end of the CAT coding region (from pCAT, Promega, Madison, Wis., USA). The 3' end of the CAT coding region was fused through an AvaI site to polio P2/P3 sequences such that translation would continue in frame from the CAT coding region through to the polio P2/P3 coding region.

The plasmid pPC(S)P (FIG. 1) was constructed to examine the effect of translation of the polio P2/P3 sequences. A pair of complementary oligonucleotides were inserted into the AvaI site, separating the P2/P3 region from the CAT coding region. These oligonucleotides encoded a stop codon and a frameshift, to ensure the termination of translation following the CAT gene. Thus, the only protein produced from this plasmid should be CAT. Plasmid pPCS (FIG. 1) consisted of the polio 5'UTR with the CAT coding region, as with pPCP and pPC(S)P, but the polio P2/P3 region was replaced with an SV40 virus 3'UTR/polyadenylation signal, obtained from pCAT (Promega). This construct was designed as a control for the effect of the polio P2/P3 region as a non-coding 3'UTR. Finally, to determine the efficiency of the polio 5'UTR, it was replaced with the 5'UTR from the CAT gene (PCCS, FIG. 1).

Example 2

This Example illustrates transient transfection of mammalian cells by the plasmids.

The plasmids prepared as described in Example 1 (15 μg DNA), were transfected into Vero cells using a standard calcium phosphate technique (ref. 16). In addition, control plasmids of either the backbone used for construction (pGEM7Zf(−)) or the high-expressing pCMV-CAT construct (Promega, Madison, USA) were similarly transfected in each experiment. As controls for transfection efficiency, 5 μg pCH110 (Pharmacia, Baie d'Urfe, PQ, Canada), a plasmid encoding β-galactosidase, was included in each transfection. The cells were grown and maintained in media pre-adsorbed with charcoal to remove glucocorticoids (ref. 15). Twenty-four hours after transfection, the cells were washed with fresh media. Transcription of one plate of cells was induced by the addition of $CdCl_2$ and dexamethasone to a final concentration of 5 μM and 1 μM respectively to induce transcription from the SG2 promoter while another was left in a non-induced state as a control.

Twenty four hours after induction the cells were harvested. Extracts were prepared and assayed for both CAT and β-galactosidase activity. β-galactosidase results were used to normalize the CAT activity for transformation efficiency. Within any one experiment there was no significant difference in β-galactosidase activity, regardless of the construct used, or the presence or absence of transcriptional activator (data not shown). Results of the normalized CAT assays are shown in the upper (A) panel of FIG. 2, as the mean CAT activity of three experiments (arbitrary phosphorimager units), with the standard error of the mean indicated. A representative example of a single assay aligned with the histogram is shown in the lower (B) panel of FIG. 2.

As anticipated, extracts prepared from cells which had been transfected with the control plasmid pCMV-CAT (construct B, FIG. 2) displayed marked, constitutive CAT activity. By comparison, extracts prepared following transfection with the negative control, pGEM7Zf(−) (construct A, FIG. 2) displayed no activity.

The plasmids pPCS and pCCS do not encode the replication proteins of the P2/P3 regions. The RNA from these constructs will, therefore, not replicate in the transfected cells. Addition of $CdCl_2$ and dexamethasone induced minimal CAT activity in cells transfected with pPCS. The replacement of the polio 5'UTR with that of CAT (pCCS) led to a significant increase, both in the background (non-induced) and inducible activity. Thus, in transfected cells, the polio 5'UTR was less efficient that the CAT 5'UTR, despite its ability to allow cap independent initiation of translation (refs. 7, 17).

To determine if the message could be exported from the nucleus without a 3'UTR and polyadenylation site, the SV40 3'UTR/polyadenylation signal (present in pPCS and PPCCS) was replaced with the polio replicon, separated from the CAT coding region with a stop codon/frameshift (pPC(S)P). Activity from the transfected cells was similar to that seen for those transfected with pPCS, both for the induced and non-induced samples. As an untranslated sequence, the polio replicon had no detrimental (or beneficial) effect compared to the SV40 3'UTR/polyadenylation signal sequence.

However, when the stop codon was removed and the P2/P3 proteins were translated (pPCP), the induced CAT activity was similar to that obtained with induced pCCS, and greater than obtained from the other plasmids containing polio sequences (FIG. 2). This result demonstrates that active "replicon" activity could be produced following transient transfection with plasmid DNA. The activity of this construct cannot be ascribed to efficiency of the 5'UTR, since the activity obtained with pPCS was so low, or to the presence of the P2/P3 RNA sequences following the CAT coding region, since the activity obtained with pPC(S)P was also low. Accordingly, translation of the P2/P3 proteins led to RNA replication and accounted for the observed increase in the amount of the translated CAT protein.

The efficiency of the replicon system can be seen in that the level of expression from this construct, even when transcription was not induced, was higher than that observed following induction of cells transfected with pPCS or pPC(S)P. This result suggests that the small amount of RNA produced from the uninduced SG2 promoter was sufficient to mediate synthesis of and serve as a substrate for viral replication machinery.

Replacing the SG2 promoter in the pPCP and pPC(S)P constructs with a bacteriophage in vitro transcription promoter allowed visualisation of the products of transcription and translation of these gene fusions in vitro. This experiment (data not shown) confirmed that the product translated from pPC(S)P corresponded to the size of CAT, whereas pPCP produced a much larger product, corresponding to translation of the CAT/polio P2/P3 protein fusion. Accordingly, the polio P2/P3 protein were produced form the pPCP plasmid, while the stop codon/frameshift in between the CAT and polio P2/P3 genes in pPC(S)P halted translation following the CAT coding region.

Taken together, these results suggest that RNA was being produced from the constructs, and that the RNA produced from pPCP was exported from the nucleus and was replication competent.

Example 3

This Example illustrates the stable transfection of Vero cells.

To generate stable cell lines, PPCP was co-transfected with pMAMneo (Stratagene, La Jolla, Calif., USA), a plasmid harbouring a neomycin resistance gene, into Vero cells. The cells were grown in G418 (Gibco, Burlington, Ont., Canada) containing media, and surviving colonies were selected and assayed for the presence of the CAT coding region within the chromosomal DNA by PCR and for CAT activity using oligonucleotides designed to anneal to the polio 5'UTR sequence, upstream of the CAT gene, and to the polio P2/P3 sequence, downstream of the CAT gene. Of the six colonies, four contained the CAT gene (data not shown). Positive colonies were expanded and subcultured through several passages up to 20 times.

At times during the passaging, samples of the cells were taken and plated. Transcription of the replicon sequences was induced and the cells were harvested and assayed for CAT activity at different times. FIG. 3 shows a representative result from cells which were passaged 6 times (A) or 20 times (B). Constitutive, non-inducible CAT activity can be seen in all cases, regardless of the number of passages the cells had undergone. From this data, together with that obtained from the transient transfection experiment data presented in Example 2 and FIG. 2, it can be concluded that a stable cell line, expressing a CAT containing polio replicon, has been created. The low-level of constitutive expression from the SG2 promoter is sufficient to synthesise RNA that can be exported from the nucleus, and, after translation of the P2/P3 region, can replicate. Thus, further induction of transcription with exogenous heavy metal or steroid did not increase the levels of expression beyond the uninduced level.

Cells from different passages were assayed for CAT activity plus and minus induction using $CdCl_2$/dexamethasone, as above. Cells were harvested either immediately following this treatment, or maintained for 24, 48, 64 or 72 hours prior to harvesting (FIG. 3).

Example 4

This Example illustrates the enzymatic assay for CAT activity in Vero cell extracts.

Cell extract was prepared by subjecting the harvested cells from vector, Example 2 or 3, to three cycles of freeze/thaw using a dry ice/ethanol bath, followed by centrifugation to remove cell debris. CAT activity was assayed using a standard $^{14}$C-chloramphenicol/TLC method (ref. 16). TLC plates were exposed to a phosphorimager storage screen (Molecular Dynamics), and data obtained following scanning using Imagequant software. β-galactosidase activity, from the transient transfections, was used to take into account the efficiency of transfection for standardizing the measurement of CAT levels in each experiment. The data obtained is shown graphically in FIGS. 2 and 3.

SUMMARY OF THE DISCLOSURE

In summary of this disclosure, DNA molecules containing foreign genes and poliovirus replicon elements are constructed and included in vectors for heterologous gene expression in mammalian cells. Modifications are possible with the scope of this invention.

REFERENCES

1. Kitamura, N., Semler, B. L., Rothberg, P. G., Larsen, G. R., Adler, C. J., Emini, E. A., Hanecak, R., Lee, J. L., Van der Werf, S., Anderson, C. W. and Wimmer, E. (1981) Primary structure, gene organization and polypeptide expression of polio virus RNA. Nature 291, 547–553.
2. Racaniello, V. R. and Baltimore, D. (1981) Molecular cloning of polio virus cDNA and determination of the complete nucleotide sequence of the viral genome. Proc. Natl. Acad. Sci. USA, 78, 4887–4891.
3. Kaplan, G. and Racaniello, V. R. (1988) Construction and characterization of polio virus subgenomic replicons. J. Virology, 62, 1687–1696.
4. Percy, N., Barclay, W. S., Sullivan, M. and Almond, J. W. (1992) A polio virus replicon containing the chloramphenicol acetytransferase gene can be used to study the replication and encapsidation of polio virus RNA. J. Virol. 66, 5040–5046.
5. Rohll, J. B., Percy, N., Ley, R., Evans, D. J. Almond, J. W. and Barclay, W. S. (1994) the 5'-untranslated region of picornovirus RNAs contain independent functional domains essential for RNA replication and translation. J. Virol. 68, 4384–4391.
6. Nicholson, R., Pelletier, J., Le, S. Y. and Sonenberg, N. (1991) Structural and functional analysis of the ribosome landing pad of polio virus type 2: in vivo translational studies. J. Virol. 65, 5886–5894.
7. Pelletier, J., Kaplan, G. Racaniello, V. R. and Sonenburg, N. (1988) Cap-independent translation of polio virus mRNA is conferred by sequence elements within the 5'noncoding region. Mol. Cell. Biol. 8, 1103–1112.
8. Choi, W. S., Pal-Ghosh, R. and Morrow, C. D. (1991) Expression of human immunodefficiency virus Type 1 (HIV-1) gag, pol and env proteins from chimeric HIV-1-polio virus minireplicons. J. Virol. 65, 2875–2883.
9. Porter, D. C., Ansardi, D. C. and Morrow, C. D. (1995) Encapsidation of polio virus replicons encoding the complete human immunodeficiency virus type 1 gag gene by a complementation system which provides the P1 capsid proteins in trans. J. Virol. 69, 1548–1555.
10. Porter, D. C., Melsen, L. R., Compans, R. W. and Morrow, C. D. (1996) Release of virus-like particles from cells infected with polio virus replicons which express human immunodeficiency virus type 1 gag. J. Virol. 70, 2643–2649.
11. Anderson, M. J., Porter, D. C., Fultz, P. N. and Morrow, C. D. (1996) Polio virus replicons that express the gag or envelope surface protein of Simian Immunodeficiency virus $SIV_{smm}PBj14$. Virology. 219, 140–149.
12. Ansardi, D. C., Moldoveanu, Z., Porter, D., Walker, D. E., Conry, R. M., LoBuglio, A. F., McPherson, S. and Morrow, C. D. (1994) Characterization of polio virus replicons encoding carcinoembryonic antigen. Cancer Res. 54, 6359–6365.
13. Van der Verf, S., Bradley, J., Wimmer, E., Studier, F. W. and Dunn, J. J. (1986) Synthesis of infectious polio virus RNA by purified T7 RNA polymerase. Proc. Natl. Acad. Sci. USA. 83, 2330–2334.
14. Racaniello, V. R. and Baltimore, D. (1981b). Cloned polio virus complementary DNA is infectious in mammalian cells. Science. 214, 916–919.
15. Filmus, J., Remani, J. and Klein, M. H. (1992) Synergistic inductino of promoters containing metal- and glucocorticoid-responsive elements. Nuc. Acids. Res. 20, 2755–2760.
16. Sambrook, J., Fritsch, E. F. & Maniatis, T. (1989) Molecular Cloning: A Laboratory Manual, $2^{nd}$ edition. Cold Spring Harbour, N.Y.: Cold Spring Harbour Laboratory Press.
17. Pelletier, J. and Sonenburg, N. (1988) Internal initiation of translation of eukaryotic mRNA directed by a sequence derived from poliovirus RNA. Nature. 224, 320–325.
18. Gossen, M. and Bujard, H. (1992) Tight control of gene expression in mammalian cells by tetracyclin-responsive promoters. Proc. Natl. Acad. Sci. USA. 89, 5547–5551.

What we claim is:

1. A DNA molecule consisting of, in sequence from the 5' end to the 3' end of the molecule, an inducible mammalian promoter, at least one functional portion of a 5'-untranslated region of a poliovirus which provides replication and translation, a gene encoding a gene product heterologous to poliovirus in the location of the poliovirus replicon normally occupied by the P1 coding region. whereby the P1 coding region is absent from the DNA molecule, and at least one functional portion of the P2 and P3 coding regions and the 3'UTR region of poliovirus forming a functional replicon.

2. The DNA molecule of claim 1 wherein said inducible mammalian promoter is the human metallothionine promoter hMT-IIA having inserted therein at least two linked glucocorticoid responsive elements (GREs).

3. The DNA molecule of claim 2 wherein said linked GRE's each comprises a synthetic molecule containing the GRE consensus sequence and having a positive strand having the nucleotide sequence: 5'-GATCTTGCGCCCGGCCCG-3'(SEQ ID NO:1).

4. The DNA molecule of claim 3 wherein two native constitutive elements of hMT-IIA, AP1 and AP2, located between bases −796 and −129 of the native hMT-IIA promoter are functionally disabled.

5. The DNA molecule of claim 4 wherein the at least two GRE's are inserted at the SacII site (base −175) of the native hMT-IIA promoter, thereby disrupting a second AP2 constitutive element at that location.

6. The DNA molecule of claim 1 wherein said functional portion of the 5'-untranslated region of a poliovirus comprises the 743 nucleotides of the 5'-untranslated region of poliovirus.

7. The DNA molecule of claim 1 wherein the heterologous gene product is selected from the group consisting of proteins and peptides.

8. The DNA molecule of claim 7 wherein the protein or peptide is selected from the group consisting of an enzyme, an antigen, an immunogen, an allergen, an enzyme inhibitor, a hormone, a lymphokine, an immunoglobulin or fragment thereof, a toxin, a toxin subunit, a mammalian protein, a structural protein and a receptor.

9. The DNA molecule of claim 1 wherein the functional replicon comprises DNA encoding the P2 and P3 coding sequences of poliovirus and the 3'UTR region.

10. A vector for heterologous gene expression, comprising the DNA molecule of claim 1.

11. An expression system for heterologous gene expression, comprising mammalian cells containing the vector claimed in claim 10 for effecting expression of the heterologous gene product.

12. The expression system of claim 11 wherein said mammalian cells are selected from Vero, CHO, HeLa, RatII and epithelial cells.

13. The expression system of claim 11 wherein said mammalian cells are transiently infected.

14. The expression system of claim 11 wherein said mammalian cells are stably infected.

15. A method of effecting heterologous gene expression, which comprises:

constructing a vector as claimed in claim 10, transfecting mammalian cells with the vector, effecting expression of the heterologous gene product from the mammalian cells, and recovering the heterologous gene product.

16. The method of claim 15 wherein said cells are transiently infected by said vector.

17. The method of claim 15 wherein said cells are stably infected by said vector.

* * * * *